(12) United States Patent
Fletcher et al.

(10) Patent No.: US 6,974,424 B2
(45) Date of Patent: Dec. 13, 2005

(54) PALATOMETER AND NASOMETER APPARATUS

(75) Inventors: Samuel G. Fletcher, Springville, UT (US); Burton Sparks, Provo, UT (US); J. Matthew Tanner, Hillsboro, OR (US)

(73) Assignee: Logometrix Corporation, Glendale, AZ (US)

( * ) Notice: Subject to any disclaimer, the term of this patent is extended or adjusted under 35 U.S.C. 154(b) by 320 days.

(21) Appl. No.: 09/956,560

(22) Filed: Sep. 19, 2001

(65) Prior Publication Data

US 2002/0087103 A1 Jul. 4, 2002

Related U.S. Application Data

(60) Provisional application No. 60/233,770, filed on Sep. 19, 2000.

(51) Int. Cl.[7] .......................... A61B 5/103; A61B 5/117
(52) U.S. Cl. ..................................................... 600/587
(58) Field of Search ................................ 600/587, 300, 600/590, 24; 433/6, 125, 214, 213; 128/848, 128/859; 704/243, 275; 607/154; 379/52; 382/114

(56) References Cited

U.S. PATENT DOCUMENTS

| | | | |
|---|---|---|---|
| 3,349,489 A | 10/1967 | Schackelford |
| 3,524,932 A | 8/1970 | Stucki |
| 3,752,929 A | 8/1973 | Fletcher |
| 4,112,596 A | 9/1978 | Fletcher et al. |
| 4,175,338 A | 11/1979 | Takinishi et al. |
| 4,287,895 A | 9/1981 | Hori |
| 4,310,002 A | 1/1982 | Takinishi et al. |
| 4,334,542 A | 6/1982 | Takinishi et al. |
| 4,460,342 A | 7/1984 | Mills |
| 4,672,673 A | 6/1987 | Katz et al. |
| 4,907,602 A | 3/1990 | Sanders |
| 5,016,647 A | 5/1991 | Sanders |

(Continued)

FOREIGN PATENT DOCUMENTS

JP    50-001846    1/1975

(Continued)

OTHER PUBLICATIONS

Nasometer II, Model 6400, The Most Widely Used Clinical Tool for Assessment and Treatment of Nasality Problems, pp. 1-2.*

(Continued)

Primary Examiner—Max F. Hindenburg
Assistant Examiner—Brian Szmal
(74) Attorney, Agent, or Firm—Clayton, Howarth & Cannon, P.C.

(57) ABSTRACT

A palatometer and nasometer apparatus is disclosed for the diagnosis and treatment of speech impairment, new language sound learning, and other uses. The palatometer includes a palatal body containing electrodes which fits in a user's mouth. Contact between the user's tongue or lips and the electrodes is indicated on display equipment. The palatometer and display equipment operate to indicate the position and movement of the tongue and lips. The nasometer includes interchangeable sound separator plates to fit users with different facial curvatures. Microphones are attached to the top and bottom of the sound separator plate to measure sound emitted from the nose and mouth for determining the nasality of speech. The palatometer and nasometer are combined to optimize the ability to define speech normality as well as diagnose and remediate speech.

113 Claims, 9 Drawing Sheets

U.S. PATENT DOCUMENTS

| | | | |
|---|---|---|---|
| 5,169,316 A | 12/1992 | Lorman et al. | |
| 5,212,476 A | 5/1993 | Maloney | |
| 5,213,553 A | 5/1993 | Light | |
| 5,257,930 A | 11/1993 | Blakeley | |
| 5,326,349 A | 7/1994 | Baraff | |
| 5,340,316 A | 8/1994 | Javkin et al. | |
| 5,452,727 A | 9/1995 | Tura et al. | |
| 5,609,161 A | 3/1997 | Tura et al. | |
| 5,689,246 A | 11/1997 | Dordick et al. | |
| 5,954,673 A | 9/1999 | Staehlin et al. | |
| 6,343,269 B1 * | 1/2002 | Harada et al. | 704/243 |
| 6,430,450 B1 * | 8/2002 | Bach-y-Rita et al. | 607/134 |

FOREIGN PATENT DOCUMENTS

| | | |
|---|---|---|
| JP | 50-11505 | 2/1975 |
| JP | 53-42490 | 4/1978 |
| JP | 53-47193 | 4/1978 |
| JP | 55-131207 | 9/1980 |
| JP | 55-143146 | 11/1980 |
| JP | 55-148554 | 11/1980 |
| JP | 58-150995 | 9/1983 |
| JP | 58-150997 | 9/1983 |
| JP | 01260481 A | 10/1989 |

OTHER PUBLICATIONS

UCLA Phonetics Lab, Electropalatography (EPG), pp. 1-14.*

McMahon, Ashley, The Clinical Use of Nasometry (Kay Elemetrics Nasometer-Model 6200-3), pp. 1-3.*

Fletcher, Samuel G., *Articulation: A Physiological Approach*. Singular Publishing Group, San Diego, California, 1992.

* cited by examiner

PALATOMETER AND NASOMETER APPARATUS

CROSS-REFERENCE TO RELATED APPLICATIONS

This application claims the benefit of U.S. Provisional Application No. 60/233,770, filed Sep. 19, 2000 which is hereby incorporated by reference herein in its entirety, including but not limited to those portions that specifically appear hereinafter.

STATEMENT REGARDING FEDERALLY SPONSORED RESEARCH OR DEVELOPMENT

Not Applicable.

BACKGROUND OF THE INVENTION

1. The Field of the Invention

The present invention relates generally to devices useful in the diagnosis and treatment of speech impairment and in new language sound learning, and more particularly, but not necessarily entirely, to devices for determining the position of the tongue and determining the nasality of human speech.

2. Description of Related Art

The initiation of precise measurement technology and procedures in the nineteenth century opened the way to reproducible observations and rigorous explanatory theory in the sciences. Precise measures of tongue positions and movements were slow to develop, however, because the actions were concealed within the oral cavity and took place within a moist, chemically active environment. Phoneticians were left to personal impressions to infer what was happening as sounds were formed. Based on these inferences, they identified, inventoried, characterized, described, and classified sounds and their misarticulation. Hearing acuity, background noises, training and experience, and perceptual biases directly influenced these judgments.

In the late 1800s scientists discovered they could partially overcome their limited ability to confirm phonetic concepts by coating the palate with powder or other materials, having the person speak, then sketching or photographing where the tongue wiped the material off the palate during the sound spoken. This "palatographic" procedure was, however, restricted to single sound observations. Saying a second sound destroyed the wipe pattern. Dynamic speech remained physically inscrutable.

During the mid-1920s the sound spectrograph was invented. This instrument converted speech signals into time by frequency and intensity acoustic displays. The ability to display sound patterns brought a shift from physiology to acoustics in speech observations. Speech intelligibility, phonetic timing, coarticulation, and other phonetic entities were translated into this acoustic, listener oriented model. But the fact that acoustic output can infer only what might be happening in the mouth roused continually increasing concern. The need for information about actual articulator positions, fine cavity configurations, and three-dimensional movement patterns was increasingly recognized as imperative to both phonetic theory and practice.

The 1950s and 60s brought a serious search for ways to access the dynamic temporal and spatial qualities of speech production. X-rays, particularly cineradiology, opened this doorway. Analysis of these data was, however, fraught with problems related to key frame selection difficulties, slow and arduous hand tracing, noise from the recording camera that obscured acoustic details, bony structures occluding the tongue and other soft tissues unless radiopaque substances were used to define their margins, and, most importantly, damaging radiation that severely limited x-ray use. Computerized x-ray microbeam systems were introduced to reduce radiation by tracking lead pellets attached to articulatory structures. This extremely complex and expensive-to-implement technology reduced radiation but also limited the observations to the few points that could be tracked simultaneously.

In the 1980s magnetic resonance imaging (MRI) brought magnetic field, body-sectioning principles to speech studies. MRI's major limitations were that the subjects must be in a supine position, the measures were limited to a few samples per second, and soft tissue resolution was poor. Each of these factors compromised its use in dynamic speech observations.

Palatography was reintroduced in the 1960s using electronic technology to overcome the original single-sound observation limitations. Kusmin in Russia (Kuzmin, Yl (1962) Mobile palatography as a tool for acoustic study of speech sounds. Fourth International Congress on Acoustics, Copenhagen. Report G35) used paired electrodes to detect linguapalatal contact. Both members of his electrode pair had to be contacted simultaneously to complete the circuit. Several other investigators adopted this approach. Kydd and Belt (Kydd, W, Belt, D A (1964), Continuous palatography. Journal of Speech and Hearing Disorders. 29:489–492) used the tongue as the positive pole with twelve contact sensing electrodes on a pseudopalate in the system they developed. Both of these systems were fraught with serious signal detection and sensor-to-sensor saliva bridging problems.

In 1969 Fletcher, Berry, and Greer (see U.S. Pat. No. 4,112,596, granted Sep. 12, 1978 to Fletcher et al.) introduced the use of an AC signal to inject a body current that flowed to the tongue. When the tongue touched sensors on a pseudopalate placed in the mouth, the nonperceptable current continued through the tongue to them. The stronger current flow available in this procedure virtually eliminated saliva bridging and, in turn, significantly increased the potential density of the sensor sampling points. Precise definition of intraoral contact place, area and contour thus became feasible and was adopted by other investigators. The unique ability to identify and track articulation placement and movement and provide detailed information about dynamic action patterns at the precise locations and moments when critical speech production events were transpiring during rapid, intricate articulatory sequences was now available electropalatometrically.

The nasometer is a second major part of speech therapy and new language sound learning, next to the palatometer. Since its invention in the 1960s by Fletcher and his associates, the nasometer has become the most used instrument in the world for assessing and modifying abnormal nasal resonance (see U.S. Pat. No. 3,752,929, granted Aug. 14, 1973, to Fletcher). It detects, measures, and compares sound from the nose and mouth during speech. The measures are displayed as calculated "nasalance" acoustic intensity ratio scores within selectable bandwidths. "Nasogram" plots are used in differential diagnosis of nasality abnormalities from congenital disorders such as cleft palate, progressive diseases such as myasthenia gravis, and accidents that disrupt the ability to separate oral sounds from nasal resonance. The measures are also used to guide behavioral, surgical, and/or prosthetic intervention and to assess the amount and pattern of improvement.

In the original nasometer the plate that fits against the lip to separate sound from the mouth and nose had a "one shape fits all" curvature. If not prevented, sound could then leak between the microphone channels and contaminate the resulting nasalance scores. This problem has been corrected in our improved nasometer by using facial curvature data drawn from over 200 adults and children of different ages and ethnic origin. A set of interchangeable sound separation plates developed from these data effectively spans the human facial curvature range and optimizes inter-microphone sound isolation.

Our current invention, the Fonometer, brings the ability to tap a human's full capacity for fine tongue control and manipulation combined with new measurement technology and procedures. We have devised means of combining palatometry with other new instrumental devices that optimize the ability to define speech normality as well as diagnose and remediate speech abnormalities. Additionally, we have introduced means and procedures for using the Fonometer in tongue mobility testing and strengthening activities, in tongue driven external device control.

Despite the advantages of the prior art devices, the present invention provides numerous improvements described herein.

BRIEF SUMMARY AND OBJECTS OF THE INVENTION

It is therefore an object of the present invention to provide a palatometer and nasometer apparatus which optimizes the ability to define speech normality as well as diagnose and remediate speech abnormalities.

It is another object of the present invention to provide a palatometer and nasometer apparatus useful in the diagnosis and treatment of speech impairment and new language sound learning which is simple in design and manufacture.

It is another object of the present invention to provide a palatometer and nasometer apparatus which can be constructed to exact requirements.

It is another object of the present invention to provide a palatometer and nasometer apparatus which can provide reliable results on people with varied facial curvatures.

It is a further object of the present invention to provide a palatometer and nasometer apparatus which can be easily positioned to provide consistent measurements.

The above objects and others not specifically recited are realized in a specific illustrative embodiment of a palatometer and nasometer apparatus. The palatometer device includes a flexible printed circuit with electrodes for detecting the position of the tongue placed in an exact configuration. The nasometer includes a set of interchangeable sound separator plates. Microphones are attached to the sound separator plates to allow consistent positioning and measurements.

Additional objects and advantages of the invention will be set forth in the description which follows, and in part will be apparent from the description, or may be learned by the practice of the invention without undue experimentation. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which.

DETAILED DESCRIPTION OF THE INVENTION

Figure 1:
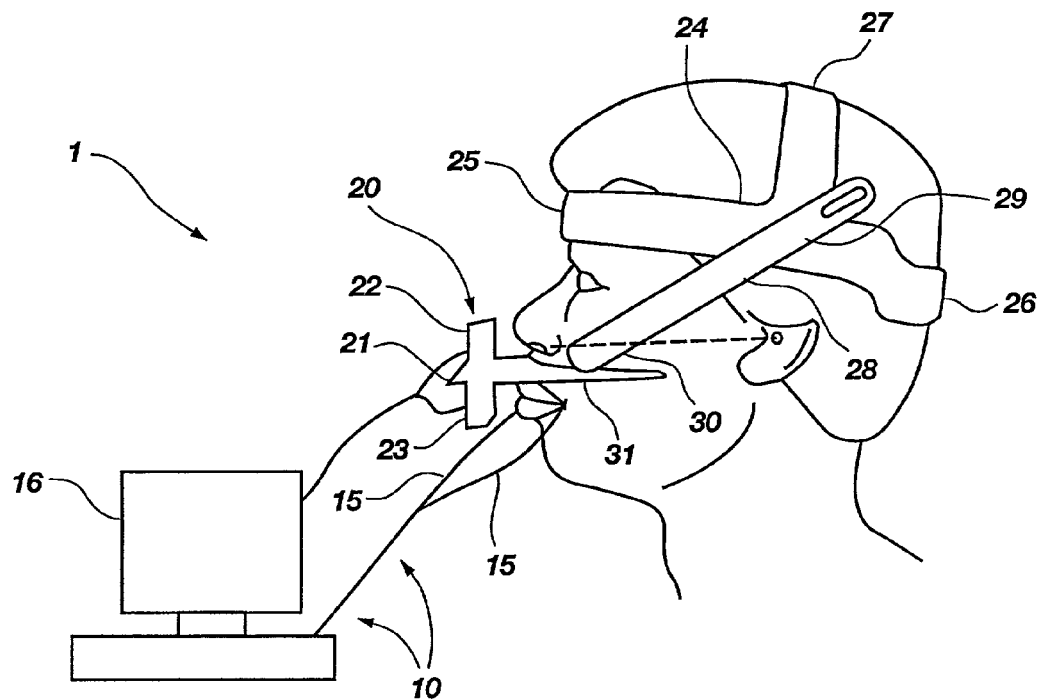
FIG. 1 is a perspective view of the palatometer and nasometer system in use, made in accordance with the principles of the present invention.

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed.

Referring now to the drawings for a better understanding of our invention, we show in FIG. 1, a perspective view of the fonometer 1, the fonometer 1 including a palatometer 10 and nasometer 20. The palatometer 10 and nasometer 20 are preferably electronically connected to suitable signal processing and display equipment 16, to operate collectively as a fonometer and thereby optimize the ability to define speech normality as well as diagnose and remediate speech abnormalities. The palatometer 10 generally comprises a palatal body, contained in the wearer's mouth in FIG. 1, and the processing and display equipment 16.

Figure 2A:
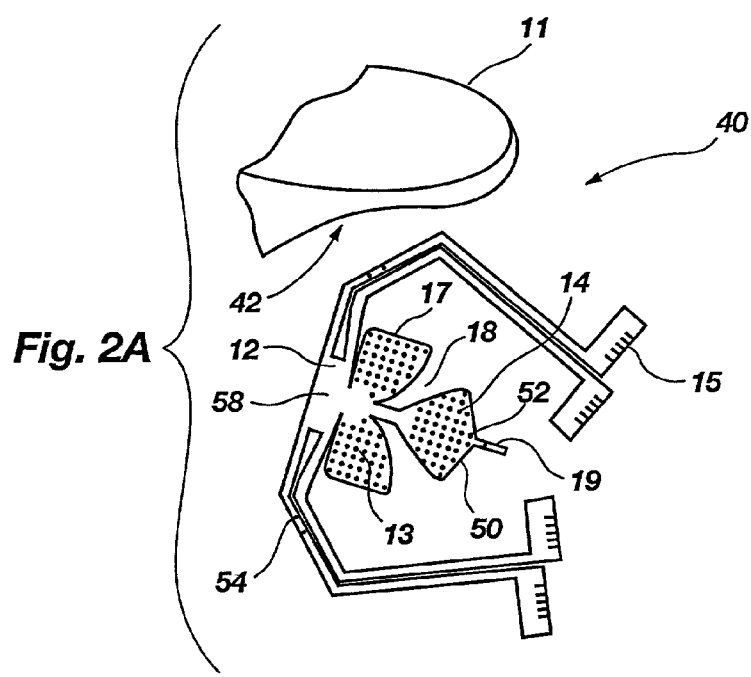
FIG. 2A is an exploded view of a palatal body of a palatometer, made in accordance with the principles of the present invention.
Figure 11:
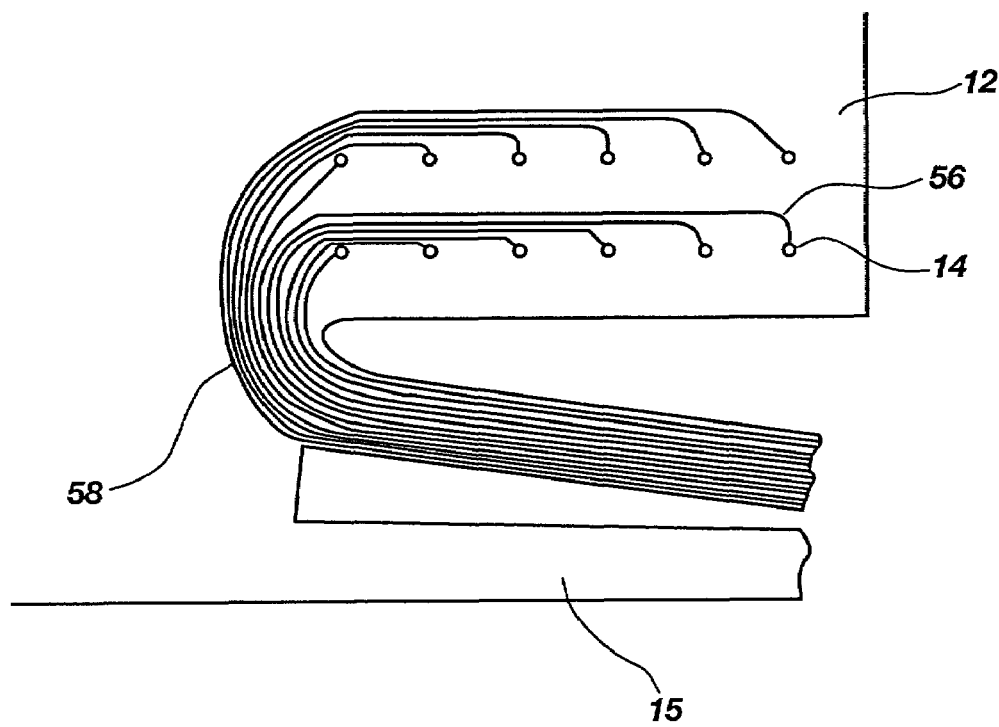
FIG. 11 is a magnified view of a portion of the flexible printed circuit of FIG. 4, showing some of the conductors connected to the electrodes.

FIG. 2A shows a first embodiment of the palatal body or pseudo palate 40 of the palatometer 10 including a base plate 11 and a flexible printed circuit 12. The base plate 11 and the flexible printed circuit 12 fit together to form the palatal body 40, as shown most clearly in FIG. 2B. The flexible printed circuit 12 includes a lingual surface 13 containing electrodes 14 spaced equidistant from each other to form a series of perpendicular rows and columns. Preferably, the spacing between the electrodes is within a range of 3.0 millimeters to 3.5 millimeters, however, other uniform electrode spacings may be used, as well as non-uniform spacing, if desired. Leads 15, containing conductors 56 which are electronically connected to the electrodes 14, may be attached to the suitable signal processing and display equipment 16. Conductors 56 extend from the electrodes away from the edge of the flexible printed circuit 12 towards a bottom central portion 58 of the flexible printed circuit 12 as shown in FIG. 11, thereby allowing the edge of the flexible printed circuit to be trimmed for sizing without disrupting the circuitry.

Figure 4:
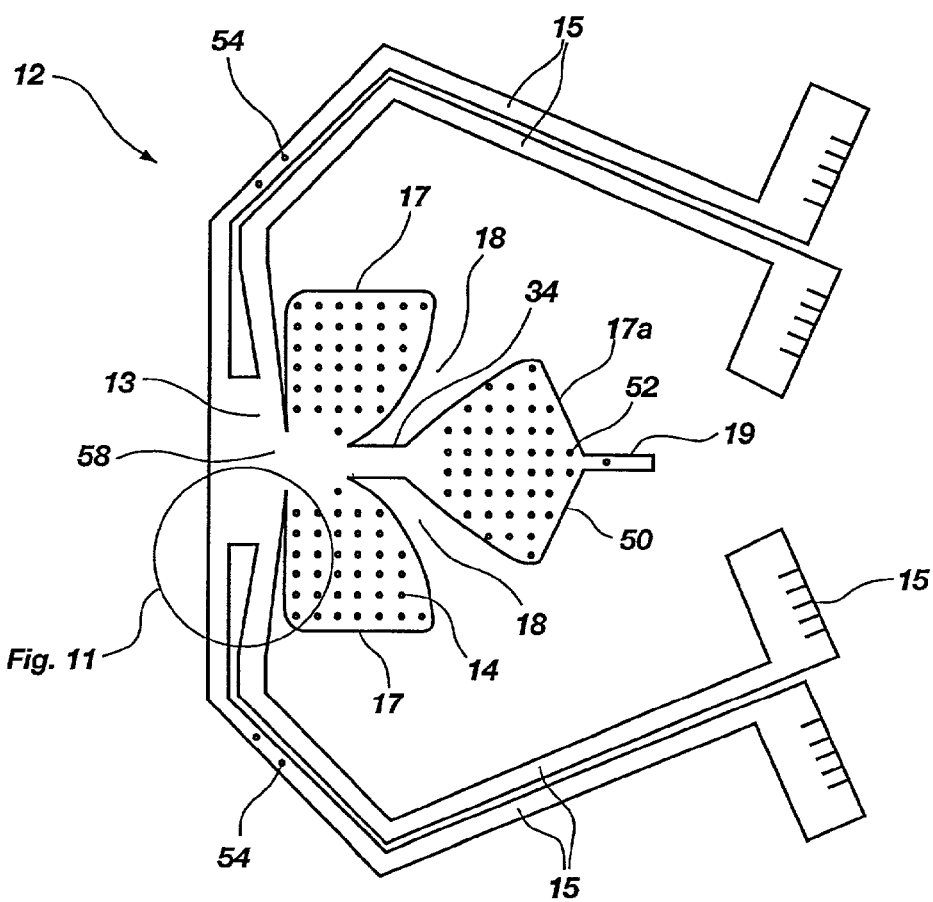
FIG. 4 is a plan view of a flexible printed circuit of the palatal body of FIG. 2A.

The electrodes 14 and conductors 56 are placed on the flexible printed circuit 12 by manufacturing machinery and can therefore be placed in an exact and rapid manner in comparison to the prior art method of manual placement of the electrodes and conductors. As shown in FIG. 4, the flexible printed circuit 12 is flat prior to installation and contains three intercoupled lobes 17, 17a. The intercoupled lobes 17, 17a have substantially equal surface areas which allow the placement of multiple electrodes on each lobe. Each lobe 17, 17a has an area greater than approximately 25% of the total area of the flexible printed circuit 12 which is covered by the electrodes 14, defined as the total electrode coverage area. The lobes 17, 17a are intercoupled to the flexible printed circuit through a narrowed side connection and are separated by uniquely shaped side-spaces 18 which allow proper molding of the flexible printed circuit. Side-spaces 18 extend far enough into the flexible printed circuit 12 to allow the flexible printed circuit to be formed into a concave configuration without creasing. A spatially separate center lobe 17a is connected to the flexible printed circuit through a neck portion 34. A width of the neck portion 34 is less than a length of the neck portion 34. The width of the neck portion 34 is also less than an average length and width of the center lobe 17a. The unique butterfly shape of the flexible printed circuit 12 enables the flexible printed circuit to conform to the shape of an undersurface 42 of the base plate 11 (which is generally in the shape of a human palate), and allows advantageous placement of the electrodes. The flexible printed circuit 12 is able to conform to palates of almost all sizes and shapes because for smaller palates, the lobes 17, 17a can be bent closer together. For larger palates, the lobes 17 17a can be maintained further apart.

A labial sensor 19 is located on the flexible printed circuit that covers the inner and outer surfaces of the incisors. This enables the sensing of labial movement as well as the sensing of lingua-dental contact between the tongue and the portion of labial sensor 19 corresponding to some portion of the teeth.

Figure 2B:
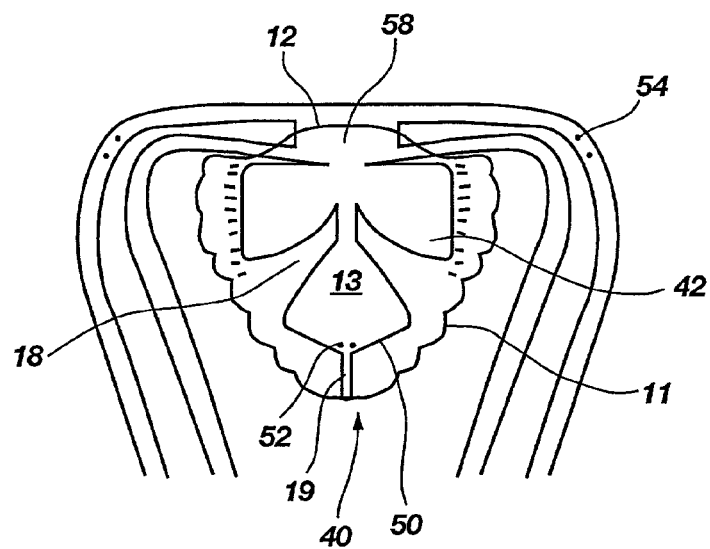
FIG. 2B is an assembled view of the palatal body of FIG. 2A.

The first embodiment of the palatal body is manufactured by first taking an impression of a user's palate using known dental procedures. The impression, or a stone model constructed from the impression, is prepared for a standard dental thermoforming process whereby a preliminary base plate 11 is formed. The base plate 11 is then cut to size and prepared for receiving the flexible printed circuit 12. The flexible printed circuit 12 is attached to the base plate 11 using a suitable adhesive such as cyanoacrylate adhesive, or other suitable adhesive. As the flexible printed circuit 12 is attached to the base plate 11, the flexible printed circuit 12 is deformably shaped from its initial flat configuration to conform to the shape of the undersurface 42 of the base plate 11 as shown in FIG. 2B. The user is then fitted with the palatometer palatal body 40 for final adjustment.

The flexible printed circuit 12 is fabricated as a thin, flat, mass-produced unit in several standard sizes. Comfort, retention, and natural configuration of the palatal body 40 in the mouth is achieved by constructing the base plate 11 using a soft plastic material that heat conforms to the user's dentition-palate arch shape and bonds with the flexible printed circuit to produce a palatal body 40 of preferably less than 0.5 mm thickness. When the flexible printed circuit 12 is bonded to the base plate 11 and pressed into the palatal arch impression from a user, its shape conforms closely to the natural surface and configuration of the user's oral structures. Preferably, the electrode grid pattern extends to the back of the furthest molars, the top sides of the center lobe 17a extend along the lower surface of the incisors, and the sides of the lobes 17 extend along the gum line. Also, the flexible printed circuit 12 is preferably configured to not cover the teeth without assuring protection of the circuitry from damage due to grinding of the teeth. The palatal body 40 and flexible printed circuit 12 are made of materials that are capable of withstanding the environment of the mouth, cleaning, and application of voltages over an extended period of time. In addition, the materials must not adversely affect the user.

Figure 8:
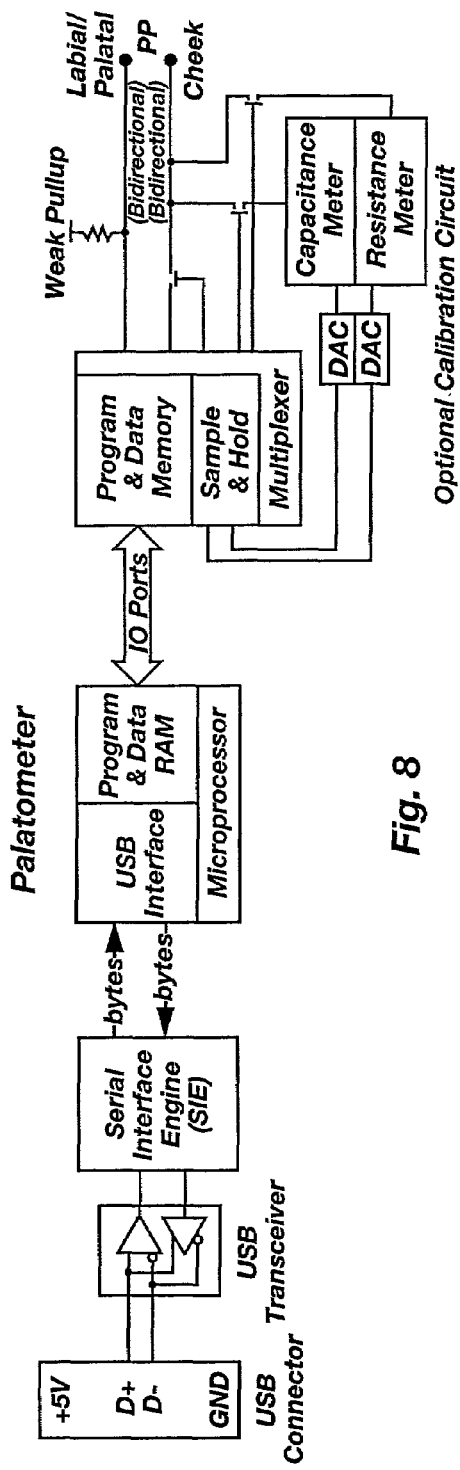
FIG. 8 is a schematic view of one of several possible embodiments of a circuit arrangement used to enable the palatometer of the present invention.

The configuration of the flexible printed circuit 12 is designed such that the molding process brings its sensors into a standardized x-y grid at preestablished distances apart. This enhances its use in phonetic contact measurements. Preferably, at least one hundred and ten (110) sensors extend across the lingual surface 13. When the palatal body 40 is molded into place, the outer edges 50 of the sensor field extend down to the inner surfaces of the teeth. The teeth are located within the video display as though looking upward from the tongue, such that their positions are defined accurately with respect to sensor locations. This enables the teeth to serve as natural orienting landmarks as the learner focuses on precisely what is happening as sounds are formed. The most forward electrodes, other than the labial sensor, are the linguadental sensors 52. The linguadental sensors 52 are preferably positioned approximately 2 millimeters from the incisor edge of the base plate 11, which is the location corresponding to the biting edge of the wearer's incisors, to ensure that the position of the flexible printed circuit 12 on the base plate 11 causes the electrodes 14 to reside in a position relative to the wearer's mouth and teeth in manner to be illustrated on the display equipment 16. When positioned in this manner, the representations of the lingual contact on the display monitor quantitatively corresponds with the actual lingual contact with the electrodes. Several possible embodiments of a circuit arrangement may be used to enable the palatometer 10 of the present invention, one of which is shown in FIG. 8.

Figure 12:
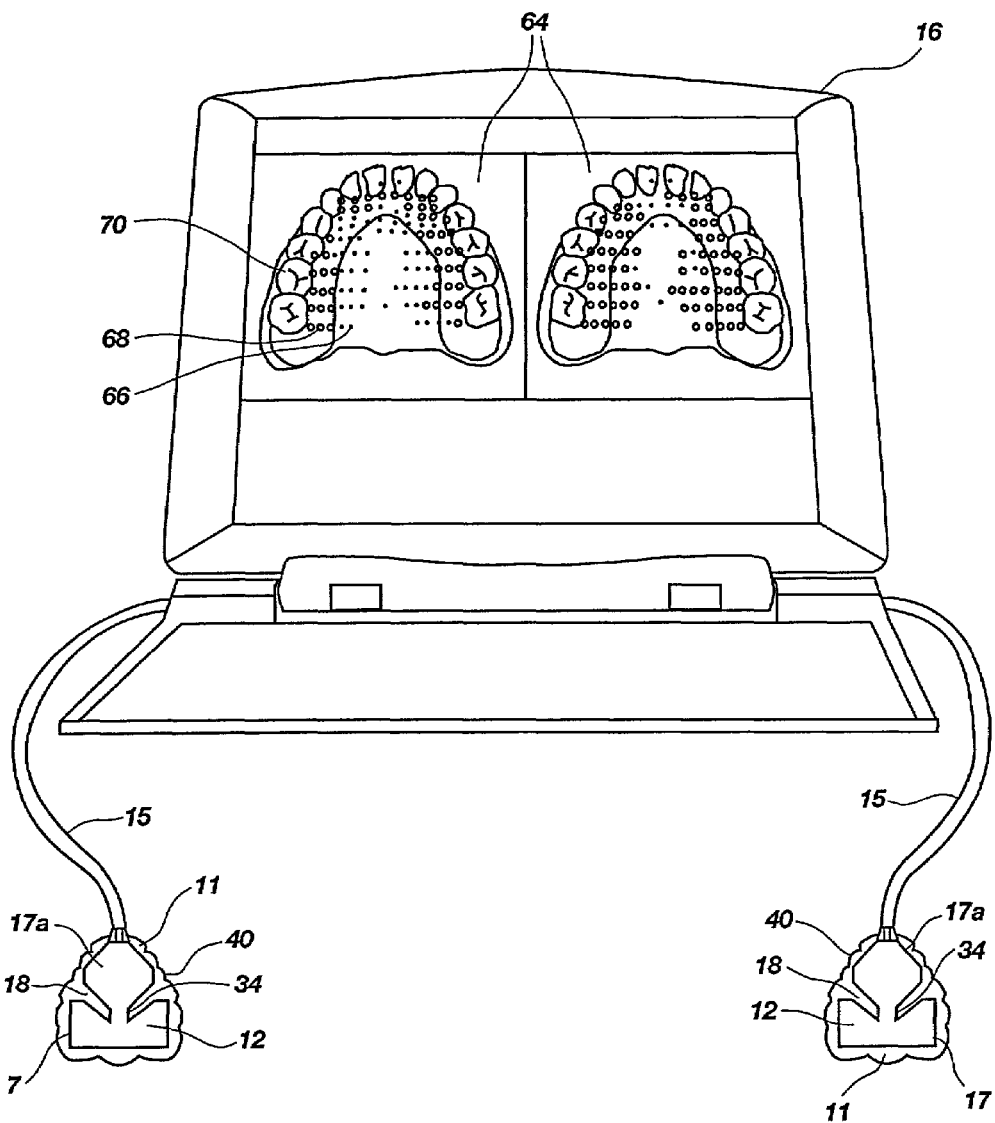
FIG. 12 is a perspective view of an embodiment of the signal processing and display equipment, of the present invention, having a split screen.

A preferred embodiment of the signal processing and display equipment 16 is shown in FIG. 12. The display is preferably configured in a split screen 64 so that two representations can be shown at the same time. Prior to contact, the electrodes 14 are preferably shown on the monitor as small black dots 66 within a grid array. The dots 66 are located on the screen such that their placement is accurately portrayed with respect to the dental and palatal configurations. Dental landmarks 70 are represented as though the observer is looking upward from the tongue. The dental landmarks 70 thus serve as natural orienting landmarks to help the observer focus on precisely how, when, and where articulation actions transpire in the mouth as different sounds are modeled and articulated. Images of the dots 66 are preferably expanded in size and the colors changed to blue to indicate sensor contact as indicated at 68. Each of the expanded dots 68 represent contact with a corresponding electrode 14, thus the boundaries, extent, and areas of contact can be quantified.

Figure 5:
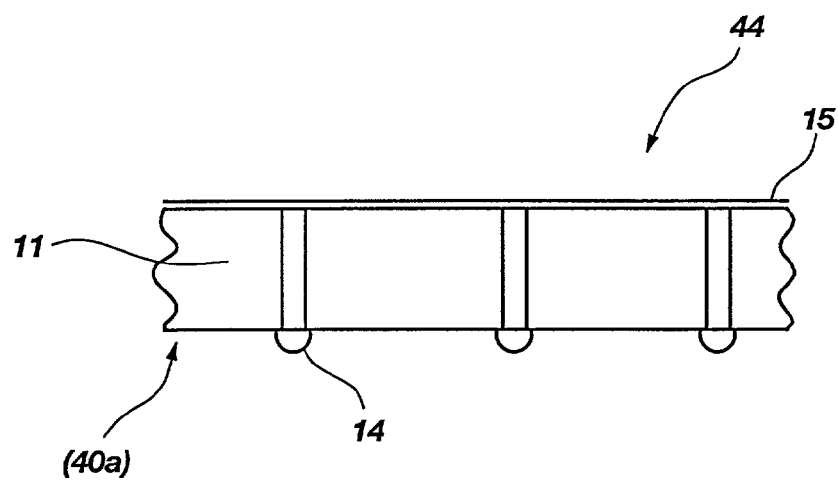
FIG. 5 is a broken, cross sectional view of an alternative embodiment of the palatal body of FIGS. 2A and 2B, in the form of a one-piece palatal body.

A second embodiment of the palatal body, designated generally at 44 is shown in FIG. 5. The second embodiment of the palatal body 44 is similar to the first embodiment 40 except that the palatal body 40a is a one-piece member. A separate flexible printed circuit is not used, rather, the electrodes 14 and conductors 56 are placed by machinery directly on a low temperature thermoplastic base plate 11. Similar to the first embodiment, a stone impression is taken of the user by a dental lab. The base plate 11 is then thermoformed over the stone impression to form the palatal body. The palatal body 44 is then cut to size and fitted for the user.

Figure 10:
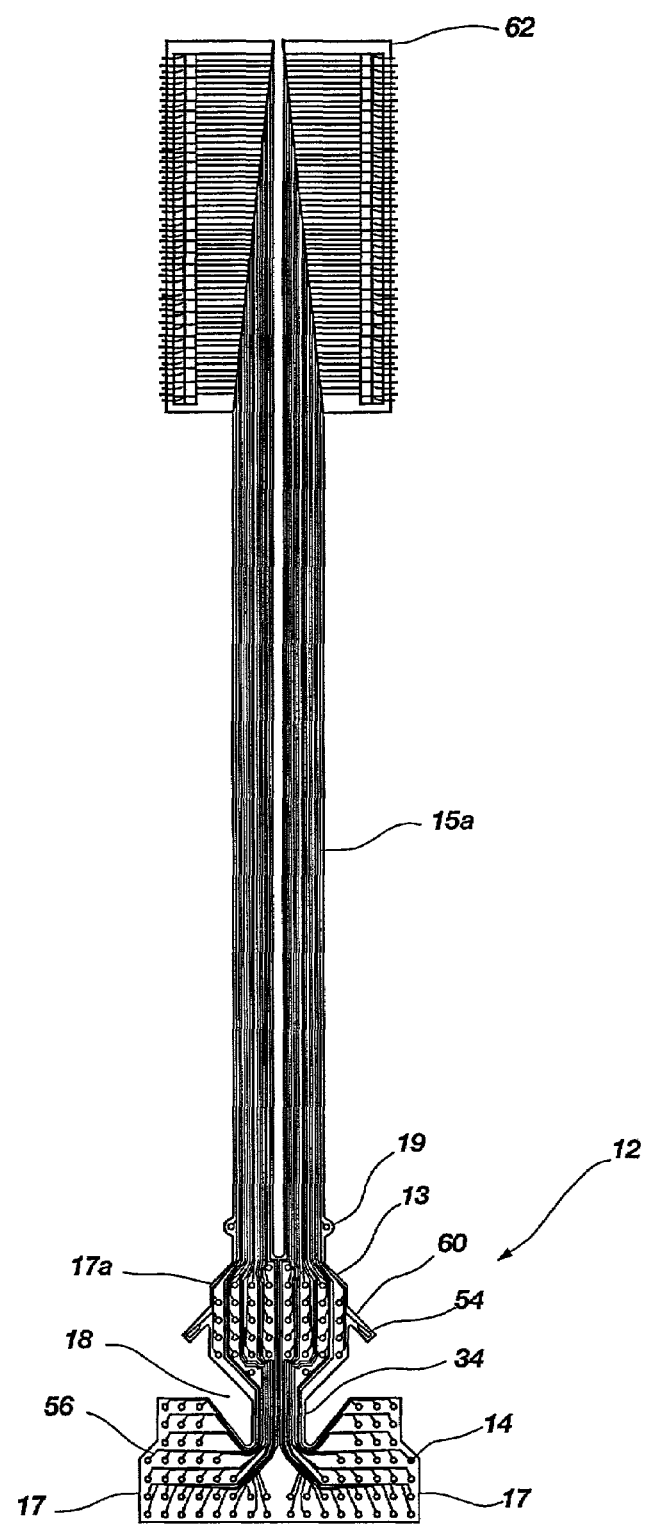
FIG. 10 is a plan view of an alternative embodiment flexible printed circuit of the palatal body showing the lead lines extending from the front.

Reference will now to made to FIG. 10 to describe an alternative embodiment of the flexible printed circuit. As previously discussed, the presently preferred embodiments of the invention illustrated herein are merely exemplary of the possible embodiments of the invention, including that illustrated in FIG. 10.

It will be appreciated that the alternative embodiment of the flexible printed circuit illustrated in FIG. 10 contains many of the same structures represented in FIGS. 2A, 2B, and 4, and only the new or different structures will be explained to most succinctly explain the additional advantages which come with the embodiments of the invention illustrated in FIG. 10. The alternative embodiment of the flexible printed circuit 12 includes leads 15a extending from a front portion of the center lobe 17a. The leads 15a contain electrical connectors 62 for connecting the flexible printed circuit 12 to processing and display equipment 16. The configuration of leads 15a is more space efficient since the leads extend directly out the front of the flexible printed circuit rather than wrapping around from the back. This configuration allows for the placement of additional electrodes along the back of the flexible printed circuit and is less invasive for the user. Leads 15a are less cumbersome since they do not impact the corners of the mouth allowing the user to speak more easily.

Also shown in the embodiment of FIG. 10 are contact points 54 used to provide a constant electrical path to ground. Contact points 54 may be located on tabs 60 which are preferably inserted into slots in the palatal body 40. The tabs 60 are then folded flush with the palatal body 40 so that the contact points 54 are located on the opposite side of the palatal body 40 as the electrodes 14.

In use, the palatal body 40 or 44 is fitted in a speaker's mouth, the leads 15 exit the mouth and are attached to the processing and display equipment 16. The electrodes 14 are specifically designed, located, spaced and shaped to be contacted by the tongue and lips, or should be contacted by the tongue and lips if the patient speaks properly. In the earlier system described in U.S. Pat. No. 3,752,929, a continuous source of current was provided to the tongue via electrodes attached to the patient's body. The circuit was completed when the tongue touched one or more of the pseudopalate electrodes. In our current system described herein, electrical current is preferably pulsed through the electrodes 14 on the palatal body 40 at 200 Hz intervals. The current applied to each electrode is limited to protect the user. The circuit is then extended to ground when the current flows through the tongue upon contact of the tongue to the electrodes 14. Each palatal body has preferably four contact points 54 used to provide a constant electrical path to ground. The present arrangement thus enables the palatometer 10 to sense the near exact location of the tongue based on the electrodes 14 contacted. Any suitable manner of sensing responsive to ground flow know to those of ordinary skill in the art may be used within the scope of the present invention. Any bridging between the electrodes that is caused by saliva is read as a higher voltage due to the difference in resistance between the tongue and the saliva. Therefore, the electrical circuitry must be properly chosen to differentiate between the resistance of saliva and the tongue. Also, the palatal body 40 is coated with a substance, preferably wax, to prevent saliva from pooling on the surface.

As the patient or new language sound learner utters or attempts to utter specifically designated sounds or words, the pattern of speech, dependent upon the contact of the tongue with the electrodes 14, is reflected in a display. The display may be shown to the patient or a clinician for corrective purposes.

Figure 3:
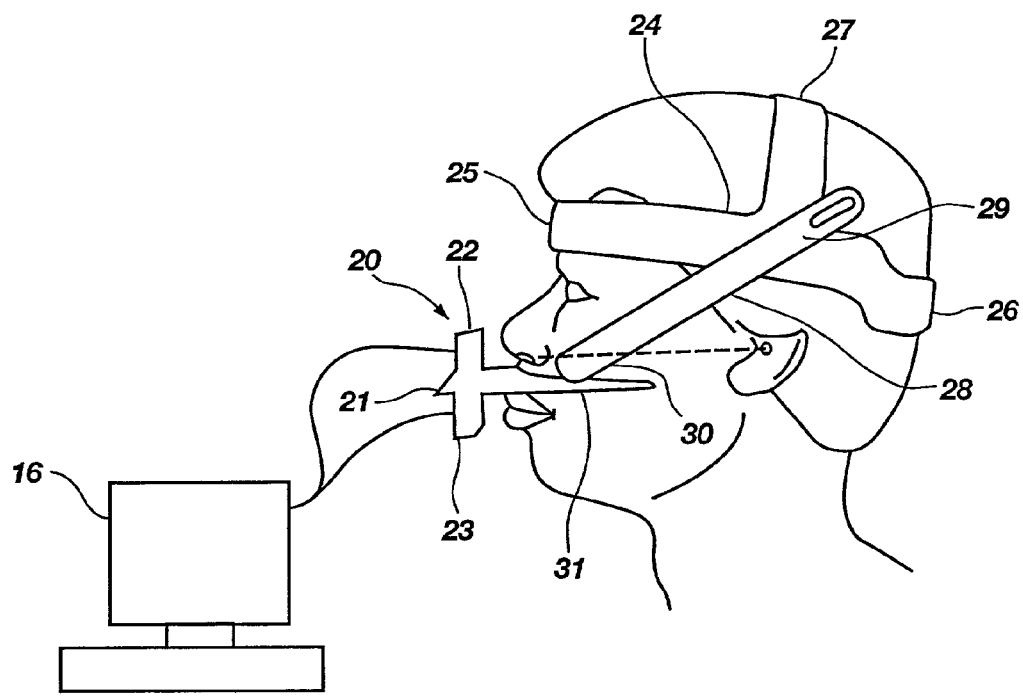
FIG. 3 is a schematic view of a nasometer, made in accordance with the principles of the present invention.

FIG. 3 shows the nasometer 20 including a sound separator plate 21, microphones 22, 23, and processing and display means 16 for processing the electronic signals produced by the signal means to render a display. The microphones 22 and 23 are left open rather than being enclosed by a housing so that resonance contamination is prevented.

A harness 24 is used to hold the sound separator plate in place. Harness 24 has a horizontal strap 25 including means 26 for securing the harness on a person, such as VELCRO hook and loop fasteners. A top adjustment band 27 is used to adjust the elevation of the harness 24. A positioning strap 28 connects the sound separator plate 21 to the horizontal strap 25 and top adjustment band 27. An upper adjustment knob 29 and lower adjustment knob 30 allow adjustment of the sound separator plate 21 on the harness 24. The positioning strap 28 also includes a snap 31 or other suitable means for connecting the sound separator plate 21 to the harness 24.

Figure 9:
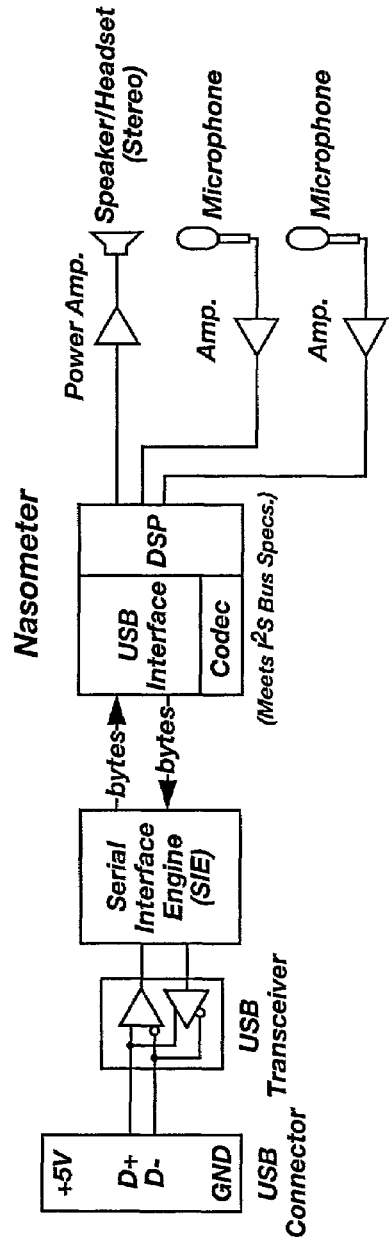
FIG. 9 is a schematic view of one of several possible embodiments of a circuit arrangement used to enable the nasometer of the present invention.

Sound emitted by the user's nose is received by the top microphone 22, whereas sound emitted by the user's mouth is received by the bottom microphone 23. A display of the sounds made by a user can be used to determine the nasality of the user's speech. Several possible embodiments of a circuit arrangement may be used to enable the nasometer of the present invention, one of which is shown in FIG. 9.

The position of the sound separator plate 21 and the microphones 22 and 23 impacts the nasalance measurements in that if the microphones are placed at different locations with respect to the nose and mouth, different measurements are obtained. Therefore, the microphones 22 and 23 are attached to the sound separator plate 21 so that the location of the microphones with respect to the sound separator plate 21 remains constant. The microphones 22 and 23 can be fixedly attached to the sound separator plate 21 or removably attached to the sound separator plate 21 so that the same microphones can be used as sound separator plates of different shapes are interchanged.

Figure 7C:
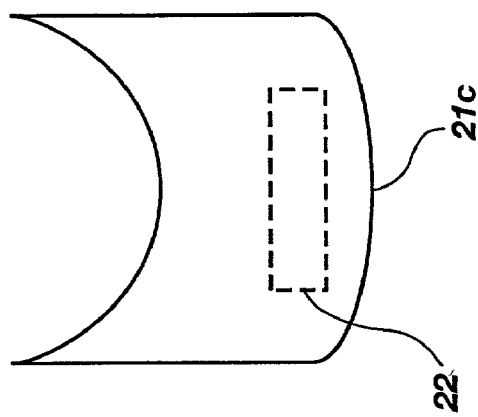
FIG. 7C is a plan view of another alternative embodiment of the sound separator plate of FIG. 7A.
Figure 7B:
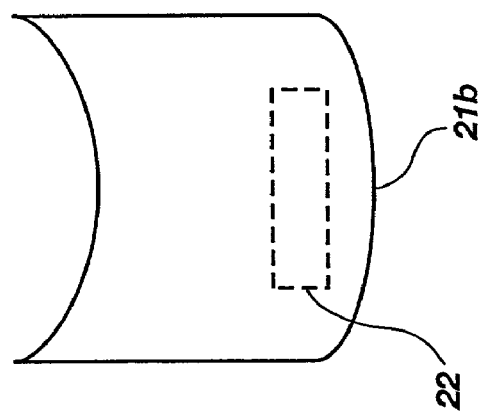
FIG. 7B is a plan view of an alternative embodiment of the sound separator plate of FIG. 7A.
Figure 7A:
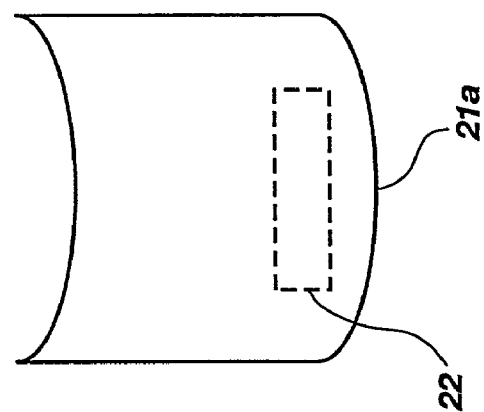
FIG. 7A is a plan view of a sound separator plate.

FIGS. 7a–7c show three different separator plates 21a, 21b, 21c with a range of curvatures to conform to the horizontal shape of the anterior maxillary bone behind the user's upper lip. The separator plates are interchangeable and can be removably attached to the nasometer by snapping them on harness 24 so that the nasometer more closely fits the particular curvature of the user's face.

Figure 6:
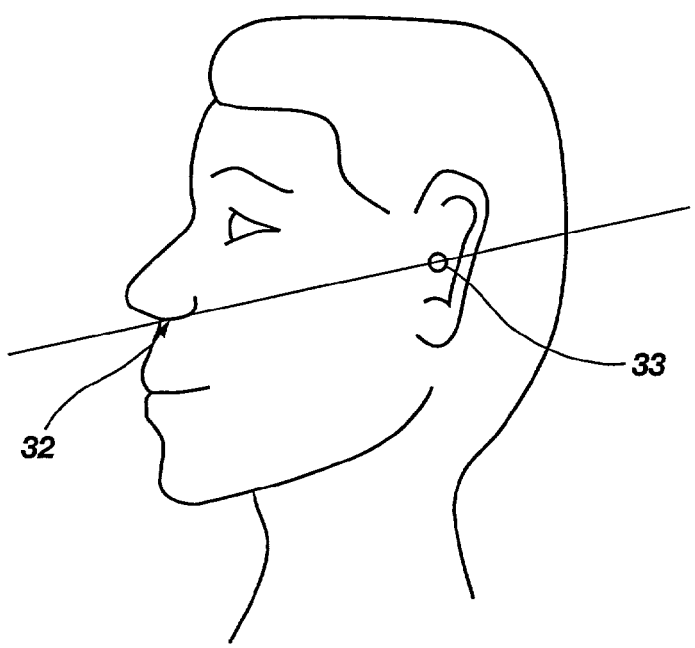
FIG. 6 is a schematic view of the ANS-P plane.

The second problem overcome in our improved nasometer 20 relates to positioning the sound separator plate 21 between the microphones 22 and 23. Historically, the sound separator plate 21 has been placed against the center of the speaker's upper lip and rotated to a position perpendicular to the person's facial plane. Some positioning errors would result in nasalance score variation attributable to the difference in positioning. This was difficult to prevent because the front of the face is curvilinear and often varies strikingly from person-to-person and race-to-race. This has led to the development of a new reference plane that extends from the maxillary anterior nasal spine (ANS) 32 at the base of the nose to an anthropometric point, Porion, (P) 33 at the center of the outer ear canal as shown in FIG. 6. To bring the sound separator plate 21 to this plane, the operator simply places the curved edge of the sound separator plate 21 against the center of the speaker's upper lip, then rotates it to parallel the standardized, straight-line ANS-P reference plane. Comparisons between data from this highly repeatable procedure and those from the facial plane reference indicated that measurement validity and reliability were significantly improved through use of the new plane. These improvements represent a major step forward in nasometric technology.

As an alternative method, the speaker's head can be oriented in a vertical position such that both porion 33 are in a desired position, preferably on the same horizontal anatomical plane. Then the operator locates the ANS-P line from one of the porion 33 and adjusts the sound separator plate 21 to be parallel to the ANS-P line.

It will be appreciated that the structure and apparatus disclosed herein are merely examples of means for performing certain functions, and it should be appreciated that any structure, apparatus or system which performs functions the same as, or equivalent to, those disclosed herein are intended to fall within the scope of a means for performing the function, including those structures, apparatus or systems for performing the function which are presently known, or which may become available in the future. Anything which functions the same as, or equivalently to, a means for performing the functions described herein falls within the scope of these elements.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A fonometer comprising:
   palatometer means for indicating the position and movement of a tongue and lips;
   nasometer means for determining the nasality of speech; and
   means for processing output from the palatometer and nasometer for display.

2. The fonometer of claim 1 wherein the palatometer means comprises a palatal body configured and dimensioned to conform generally to the palate of a person, said palatal body having a lingual surface, and a plurality of electrodes disposed on the lingual surface.

3. The fonometer of claim 2 wherein the electrodes are disposed on the lingual surface in a plurality of rows and columns, wherein said rows and columns are perpendicular to each other.

4. The fonometer of claim 3 wherein the electrodes are equidistantly spaced apart.

5. The fonometer of claim 4 wherein a spacing between the electrodes is 3.5 millimeters.

6. The fonometer of claim 2 wherein said palatal body comprises a flexible printed circuit.

7. The fonometer of claim 6 wherein the flexible printed circuit comprises a plurality of intercoupled lobes.

8. The fonometer of claim 7 wherein the plurality of intercoupled lobes comprises three lobes of substantially equal surface area.

9. The fonometer of claim 7 wherein the plurality of intercoupled lobes comprises a spatially separate center lobe intercoupled to the other lobes of the flexible printed circuit through a neck portion, a width of the neck portion being less then an average length and width of the center lobe.

10. The fonometer of claim 6 wherein the flexible printed circuit further comprises two pairs of spatially separate lead lines, each pair residing on opposite sides of the flexible printed circuit.

11. The fonometer of claim 2 wherein the palatal body is a one-piece member of unitary construction having electrodes disposed therein.

12. The fonometer of claim 2 wherein the palatal body is made of thermoformable material.

13. The fonometer of claim 6 wherein the flexible printed circuit comprises a butterfly shape.

14. The fonometer of claim 6 wherein the flexible printed circuit comprises a labial sensor.

15. The fonometer of claim 6 wherein the flexible printed circuit defines a flat orientation prior to installation on a base plate and defines an orientation conforming to the base plate when disposed on the base plate.

16. The fonometer of claim 1 wherein said palatometer means comprises means for transmitting electrical current through electrodes responsive to contact of the person's tongue or lips with said electrodes.

17. The fonometer of claim 2 wherein the palatal body comprises a base plate and a flexible printed circuit, said base plate being dimensioned to covers the person's teeth.

18. The fonometer of claim 1 wherein said nasometer means comprises a sound separator plate to separate sounds emitted from a person's nose and mouth, said separator plate being removably connected to the nasometer means such that one of a plurality of sound separator plates may be selected to conform to the person's face.

19. The fonometer of claim 1 wherein said nasometer comprises a support member having an upper side and an opposing lower side, and a first microphone attached to said upper side and a second microphone attached to said lower side.

20. The fonometer of claim 19 wherein said first microphone is removably attached to said upper side and said second microphone is removably attached to said lower side.

21. The fonometer of claim 1 wherein the nasometer means comprises a harness for holding the sound separator plate on a person.

22. The fonometer of claim 21 wherein the harness comprises a horizontal strap including means f or securing the harness on the person, an upper adjustment band for adjusting the elevation of the harness, a positioning strap for connecting to the sound separator plate, adjustment means for adjusting the position of the sound separator plate through the positioning strap, and means for connecting the sound separator plate to the harness.

23. The fonometer of claim 1 wherein the means for processing output from the palatometer and nasometer for display comprises a split screen for displaying two representations at the same time.

24. A palatometer comprising:
a palatal body configured and dimensioned to conform substantially to the palate of a person, said palatal body having a lingual surface; and
a plurality of electrodes disposed on the lingual surface of the palatal body in a plurality of rows and columns, wherein said rows and columns are perpendicular to each other;
wherein the palatal body is made of thermoformable materials;
wherein the electrodes are equidistantly spaced apart; and
wherein a spacing between the electrodes is 3.5 millimeters.

25. The palatometer of claim 24 wherein said palatal body comprises a flexible printed circuit and a base plate.

26. The palatometer of claim 25 wherein the flexible printed circuit defines a flat orientation prior to installation on the base plate and defines an orientation conforming to the base plate when disposed on the base plate.

27. The palatometer of claim 24 wherein said palatometer comprises means for transmitting electrical current through electrodes responsive to contact of the person's tongue or lips with said electrodes.

28. The palatometer of claim 25 wherein said base plate is dimensioned to cover the person's teeth.

29. A palatometer comprising:
a palatal body configured and dimensioned to conform generally to the palate of a person, said palatal body having a lingual surface; and
a plurality of electrodes disposed on the lingual surface of the palatal body in a plurality of rows and columns, wherein said rows and columns are perpendicular to each other;
wherein said palatal body comprises a flexible printed circuit and a base plate;
wherein the flexible printed circuit comprises a plurality of intercoupled lobes; and
wherein the plurality of intercoupled lobes comprises three lobes of substantially equal surface area.

30. A palatometer comprising:
a palatal body configured and dimensioned to conform generally to the palate of a person, said palatal body having a lingual surface; and
a plurality of electrodes disposed on the lingual surface of the palatal body in a plurality of rows and columns, wherein said rows and columns are perpendicular to each other;
wherein said palatal body comprises a flexible printed circuit and a base plate;
wherein the flexible printed circuit comprises a plurality of intercoupled lobes; and
wherein the plurality of intercoupled lobes comprises a spatially separate center lobe intercoupled to the other lobes of the flexible printed circuit through a neck portion, a width of the neck portion being less than an average length and width of the center lobe.

31. A palatometer comprising:
a palatal body configured and dimensioned to conform generally to the palate of a person, said palatal body having a lingual surface; and
a plurality of electrodes disposed on the lingual surface of the palatal body in a plurality of rows and columns, wherein said rows and columns are perpendicular to each other;
wherein said palatal body comprises a flexible printed circuit and a base plate; and
wherein the flexible printed circuit further comprises two pairs of spatially separate lead lines, each pair residing on opposite sides of the flexible printed circuit.

32. A palatometer comprising:
a palatal body configured and dimensioned to conform generally to the palate of a person, said palatal body having a lingual surface; and
a plurality of electrodes disposed on the lingual surface of the palatal body in a plurality of rows and columns, wherein said rows and columns are perpendicular to each other;
wherein said palatal body comprises a flexible printed circuit and a base plate; and
wherein the flexible printed circuit comprises a labial sensor.

33. A palatometer comprising:
a palatal body configured and dimensioned to conform generally to the palate of a person, said palatal body comprising a flexible printed circuit disposed on a base plate, said flexible printed circuit comprising a plurality of intercoupled lobes having substantially equal surface areas; and
a plurality of electrodes disposed on the flexible printed circuit;
wherein the flexible printed circuit comprises a labial sensor.

34. The palatometer of claim 33 wherein the electrodes are disposed a lingual surface in a plurality of rows and columns, wherein said rows and columns are perpendicular to each other.

35. The palatometer of claim 33 wherein the electrodes are equidistantly spaced apart.

36. The palatometer of claim 33 wherein the palatal body is made of thermoformable material.

37. The palatometer of claim 33 wherein the flexible printed circuit comprises a butterfly shape.

38. The palatometer of claim 33 wherein the flexible printed circuit defines a flat orientation prior to installation on a base plate and defines an orientation conforming to the base plate when disposed on the base plate.

39. The palatometer of claim 33 wherein said palatometer comprises means for transmitting electrical current through electrodes responsive to contact of the person's tongue with said electrodes.

40. The palatometer of claim 33 wherein said base plate is dimensioned to covers the person's teeth.

41. A palatometer comprising:
a palatal body configured and dimensioned to conform generally to the palate of a person, said palatal body comprising a flexible printed circuit disposed on a base plate, said flexible printed circuit comprising a plurality of intercoupled lobes having substantially equal surface areas; and
a plurality of electrodes disposed on the flexible printed circuit;
wherein the electrodes are equidistantly spaced apart; and wherein a spacing between the electrodes is 3.5 millimeters.

42. A palatometer comprising:
a palatal body configured and dimensioned to conform generally to the palate of a person, said palatal body comprising a flexible printed circuit disposed on a base plate, said flexible printed circuit comprising a plurality of intercoupled lobes having substantially equal surface areas; and
a plurality of electrodes disposed on the flexible printed circuit;
wherein the plurality of intercoupled lobes comprises a spatially separate center lobe intercoupled to the other lobes of the flexible printed circuit through a neck portion, a width of the neck portion being less than an average length and width of the center lobe.

43. A palatometer comprising:
a palatal body configured and dimensioned to conform generally to the palate of a person, said palatal body comprising a flexible printed circuit disposed on a base plate, said flexible printed circuit comprising a plurality of intercoupled lobes having substantially equal surface areas; and
a plurality of electrodes disposed on the flexible printed circuit;
wherein the flexible printed circuit further comprises two pairs of spatially separate lead lines, each pair residing on opposite sides of the flexible printed circuit.

44. A palatometer comprising:
a palatal body configured and dimensioned to conform generally to the palate of a person, said palatal body comprising a flexible printed circuit that defines a lingual surface, said flexible printed circuit comprising a labial sensor; and
a plurality of electrodes disposed on the lingual surface.

45. The palatometer of claim 44 wherein the electrodes are disposed on the lingual surface in a plurality of rows and columns, wherein said rows and columns are perpendicular to each other.

46. The palatometer of claim 44 wherein the electrodes are equidistantly spaced apart.

47. The palatometer of claim 46 wherein a spacing between the electrodes is 3.5 millimeters.

48. The palatometer of claim 44 wherein the flexible printed circuit comprises a plurality of intercoupled lobes.

49. The palatometer of claim 48 wherein the plurality of intercoupled lobes comprises three lobes of substantially equal surface area.

50. The palatometer of claim 48 wherein the plurality of intercoupled lobes comprises a spatially separate center lobe intercoupled to the other lobes of the flexible printed circuit through a neck portion, a width of the neck portion being less than an average length and width of the center lobe.

51. The palatometer of claim 44 wherein the flexible printed circuit further comprises two pairs of spatially separate lead lines, each pair residing on opposite sides of the flexible printed circuit.

52. The palatometer of claim 44 wherein the palatal body is made of thermoformable material.

53. The palatometer of claim 44 wherein the flexible printed circuit comprises a butterfly shape.

54. The palatometer of claim 44 wherein the flexible printed circuit defines a flat orientation prior to installation on a base plate and defines an orientation conforming to the base plate when disposed on the base plate.

55. The palatometer of claim 44 wherein said palatometer comprises means for transmitting electrical current through electrodes responsive to contact of the person's tongue with said electrodes.

56. The palatometer of claim 44 wherein the palatal body is dimensioned to covers the person's teeth.

57. A palatometer comprising:
a palatal body configured and dimensioned to conform generally to the palate of a person, said palatal body having a lingual surface; and
a plurality of electrodes disposed on the lingual surface of the palatal body, wherein the palatal body is a one-piece member of unitary construction;
wherein the electrodes are equidistantly spaced apart; and
wherein a spacing between the electrodes is 3.5 millimeters.

58. The palatometer of claim 57 wherein the electrodes are disposed on the lingual surface in a plurality of rows and columns, wherein said rows and columns are perpendicular to each other.

59. The palatometer of claim 57 wherein the palatal body is made of thermoformable material.

60. The palatometer of claim 57 wherein said palatometer comprises means for transmitting electrical current through electrodes responsive to contact of the person's tongue with said electrodes.

61. The palatometer of claim 57 wherein the palatal body is configured and dimensioned to conform substantially to the palate of a person.

62. A nasometer apparatus for analyzing human speech, comprising:
signal means for producing electronic signals responsive to sounds emitted from a person, said signal means including a support member having an upper side and an opposing lower side, and a first microphone fixedly attached to said upper side and a second microphone fixedly attached to said lower side;
processing and display means for processing the electronic signals produced by the signal means and rendering a display therefrom.

63. The nasometer of claim 62 wherein said first microphone is removably attached to said upper side and said second microphone is removably attached to said lower side.

64. The nasometer of claim 62 wherein said support member comprises a sound separator plate for separating sounds emitted from the person's mouth and nose.

65. The nasometer of claim 64 wherein said sound separator plate is removably connected to the nasometer such that one of a plurality of sound separator plates may be selected to conform to the person's face.

66. The nasometer of claim 64 wherein the nasometer comprises a harness for holding the sound separator plate on the person.

67. The nasometer of claim 66 wherein the harness comprises a horizontal strap including means for securing the harness on the person, an upper adjustment band for adjusting the elevation of the harness, a positioning strap for connecting to the sound separator plate, adjustment means for adjusting the position of the sound separator plate through the positioning strap, and means for connecting the sound separator plate to the harness.

68. The nasometer of claim 62 wherein said support member is characterized by an absence of a housing surrounding the microphones.

69. A nasometer apparatus for analyzing human speech, comprising:

a sound receiving means for receiving sound from nasal and oral cavities, said sound receiving means including a sound separator plate for separating sounds emitted from a nose and mouth, said sound separator plate having an upper side and an opposing lower side, said sound receiving means further including a first microphone disposed on said upper side of the sound separator plate and a second microphone disposed on said lower side of said sound separator plate, said sound receiving means being characterized by an absence of a housing surrounding the microphones; and holding means for holding the sound receiving means on the person's head.

70. The nasometer of claim 69 wherein said separator plate is removably connected to the nasometer such that one of a plurality of sound separator plates may be selected to conform to the person's face.

71. The nasometer of claim 69 wherein said first microphone is removably attached to said upper side of the sound separator plate and said second microphone is removably attached to said lower side of said sound separator plate.

72. The nasometer of claim 69 wherein the holding means comprises a harness.

73. The nasometer of claim 72 wherein the harness comprises a horizontal strap including means f or securing the harness on the person.

74. The nasometer of claim 72 wherein the harness comprises an upper adjustment band for adjusting the elevation of the harness.

75. The nasometer of claim 72 wherein the harness comprises a
a positioning strap for connecting the harness to the sound separator plate.

76. The nasometer of claim 72 wherein the harness comprises
adjustment means for adjusting the position of the sound separator plate.

77. The nasometer of claim 75 wherein the harness comprises
means for attaching the sound separator plate on the positioning strap.

78. A method of positioning a nasometer on a speaker to improve nasalence measurement reliability, the nasometer comprising a sound separator plate to separate sounds emitted from the speaker's nose and mouth, the method comprising the steps of:
(a) locating the anterior nasal spine at the base of a speaker's nose;
(b) locating outer ear canals of the speaker;
(c) locating a plane defined by the anterior nasal spine and the outer ear canals;
(d) placing the sound separator plate against the center of the speaker's upper lip;
(e) positioning the sound separator plate to cause it to reside in a substantially parallel orientation relative to the plane.

79. The method of claim 78 wherein step (e) comprises the step of positioning the sound separator plate in a substantially co-planar orientation relative to the plane.

80. The method of claim 78 wherein said separator plate is removably connected to the nasometer means such that one of a plurality of sound separator plates may be selected to conform to the speaker's face.

81. The method of claim 78 wherein said sound separator plate has an upper side and an opposing lower side, and a first microphone attached to said upper side and a second microphone attached to said lower side.

82. The method of claim 81 wherein said first microphone is removably attached to said upper side and said second microphone is removably attached to said lower side.

83. The method of claim 78 wherein the nasometer comprises a harness for holding the sound separator plate on the speaker.

84. The method of claim 83 wherein the harness comprises a horizontal strap including means for securing the harness on the speaker, an upper adjustment band for adjusting the elevation of the harness, a positioning strap for connecting to the sound separator plate, adjustment means for adjusting the position of the sound separator plate through the positioning strap, and means for connecting the sound separator plate to the harness.

85. A nasometer apparatus for analyzing human speech, comprising:
signal means for producing electronic signals responsive to sounds emitted from a person;
a sound separator plate for separating sounds emitted from the person's nose and mouth, said separator plate being removably attached to the nasometer apparatus such that one of a plurality of sound separator plates with different curvatures may be selected to conform to the person's face; and
processing and display means for processing the electronic signals produced by the signal means and rendering a display therefrom.

86. The nasometer of claim 85 wherein said sound separator plate comprises an upper side and an opposing lower side, a first microphone is attached to said upper side and a second microphone is attached to said lower side.

87. The nasometer of claim 86 wherein said first microphone is removably attached to said upper side and said second microphone is removably attached to said lower side.

88. The nasometer of claim 85 wherein the nasometer comprises a harness for holding the sound separator plate on the person.

89. The nasometer of claim 88 wherein the harness comprises a horizontal strap including means for securing the harness on the person, an upper adjustment band for adjusting the elevation of the harness, a positioning strap for connecting to the sound separator plate, adjustment means for adjusting the position of the sound separator plate through the positioning strap, and means for connecting the sound separator plate to the harness.

90. A palatometer comprising:
a palatal body configured and dimensioned to conform generally to the palate of a person and to reside in an operating position within the person's mouth, said palatal body comprising a flexible printed circuit;
a plurality of electrodes disposed on the flexible printed circuit; and
electronic lead lines connected to the electrodes and extending directly from a front portion of the flexible printed circuit when the palatal body resides in the operating position.

91. The palatometer of claim 90 wherein the flexible printed circuit is configured to be accommodated in palates having a wide range of sizes and shapes.

92. The palatometer of claim 90 wherein the spacing between the electrodes is within a range of 3.0 millimeters to 3.5 millimeters.

93. The palatometer of claim 90 wherein said palatal body further comprises a base plate, and wherein the plurality of electrodes include lingua-dental sensors disposed on the flexible printed circuit, said lingua-dental sensors are positioned on the base plate so that the position of the electrodes on the base plate corresponds to representations of the electrodes on display equipment.

94. The palatometer of claim 93 wherein said lingua-dental sensors are positioned on said base plate approximately 2 millimeters from an incisor edge of the base plate which corresponds to a biting edge of the person's incisors.

95. The palatometer of claim 90 wherein the plurality of electrodes comprises at least 110 electrodes.

96. The palatometer of claim 90 wherein the flexible printed circuit has side-spaces which extend far enough into the flexible printed circuit to allow the flexible printed circuit to be formed into a concave configuration without creasing.

97. The palatometer of claim 90 wherein the palatal body has a thickness of less than 0.5 millimeters.

98. The palatometer of claim 90 wherein the palatal body is covered with wax to prevent pooling of saliva.

99. The palatometer of claim 90 wherein the palatal body is configured and dimensioned such that at least one of the electrodes resides in continuous contact with the person's mouth to thereby operate as a contact point to provide a constant electrical path to ground with the mouth when the palatal body resides in the operating position.

100. A palatometer comprising:
a palatal body configured and dimensioned to conform generally to the palate of a person, said palatal body comprising a flexible printed circuit;
a plurality of electrodes disposed on the flexible printed circuit; and
electronic conductors connected to the electrodes and extending away from an edge of the flexible printed circuit toward a bottom central portion of the flexible printed circuit.

101. A palatometer comprising:
a palatal body configured and dimensioned to conform generally to the palate of a person, said palatal body comprising a flexible printed circuit disposed on a base plate, said flexible printed circuit comprising a plurality of intercoupled lobes and having a total electrode coverage area; and
a plurality of electrodes disposed on the flexible printed circuit;
wherein each lobe has an area greater than 25% of the total electrode coverage area.

102. A palatometer comprising:
a palatal body configured and dimensioned to conform generally to the palate of a person, said palatal body comprising a flexible printed circuit disposed on a base plate, said flexible printed circuit comprising a plurality of intercoupled lobes; and
a plurality of electrodes disposed on the flexible printed circuit;
wherein the flexible printed circuit comprises a neck portion, a width of the neck portion being less than a length of the neck portion, and wherein the intercoupled lobes are intercoupled by said neck portion.

103. A palatometer comprising:
a palatal body configured and dimensioned to conform generally to the palate of a person and to reside in an operating position within the person's mouth, said palatal body comprising a flexible printed circuit;
a plurality of electrodes disposed on the flexible printed circuit; and
position display means for displaying an illustration of physical locations of the electrodes relative to the person's palate corresponding to actual physical locations of said electrodes relative to the person's palate.

104. The palatometer of claim 103 wherein the flexible printed circuit is configured to be accommodated in palates having a wide range of sizes and shapes.

105. The palatometer of claim 103 wherein the spacing between the electrodes is within a range of 3.0 millimeters to 3.5 millimeters.

106. The palatometer of claim 103 wherein the plurality of electrodes include lingua-dental sensors disposed on the flexible printed circuit.

107. The palatometer of claim 106 wherein said lingua-dental sensors are positioned on said palatal body approximately 2 millimeters from an incisor edge of the palatal body which corresponds to a biting edge of the person's incisors.

108. The palatometer of claim 103 wherein the plurality of electrodes comprises at least 110 electrodes.

109. The palatometer of claim 103 wherein the flexible printed circuit has side-spaces which extend far enough into the flexible printed circuit to allow the flexible printed circuit to be formed into a concave configuration without creasing.

110. The palatometer of claim 103 wherein the palatal body has a thickness of less than 0.5 millimeters.

111. The palatometer of claim 103 wherein the palatal body is covered with wax to prevent pooling of saliva.

112. The palatometer of claim 103 wherein the palatal body is configured and dimensioned such that at least one of the electrodes resides in continuous contact with the person's mouth to thereby operate as a contact point to provide a constant electrical path to ground with the mouth when the palatal body resides in the operating position.

113. The palatometer of claim 102 wherein the plurality of intercoupled lobes comprises a spatially separate center lobe intercoupled to the flexible printed circuit through the neck.

* * * * *